United States Patent [19]

Wagner

[11] 4,326,548
[45] Apr. 27, 1982

[54] PERSONAL ORAL HYGIENE TOOL

[76] Inventor: Eugene C. Wagner, 3424 Kingsbridge Ave., Bronx, N.Y. 10463

[21] Appl. No.: 157,442

[22] Filed: Jun. 9, 1980

[51] Int. Cl.³ .............................................. A61C 15/00
[52] U.S. Cl. ..................................................... 132/90
[58] Field of Search .......................... 132/90, 76.2, 89; 433/147

[56] References Cited

U.S. PATENT DOCUMENTS

| 435,350 | 8/1890 | Oehlecker | 132/90 |
| 1,355,037 | 10/1920 | Dziuk | 132/90 |
| 1,527,028 | 2/1925 | Daniel | 132/89 |
| 1,723,226 | 8/1929 | Withcombe | 433/147 |
| 2,110,999 | 3/1938 | Miga | 132/76.2 X |

FOREIGN PATENT DOCUMENTS 429447  9/1911  France ................................... 132/90

Primary Examiner—Gene Mancene
Assistant Examiner—Mickey Yu
Attorney, Agent, or Firm—Natter & Natter

[57] ABSTRACT

A dental tool for personal oral hygiene includes a pen barrel shaped holder which carries a curved metal pick. The pick includes an arcuate zone ending at a tapered tip. A cap selectively covers the pick when the tool is not in use to simulate a writing implement. Opposite the tip, the pick includes a stem which is seated in the holder. The pick is formed of a stainless resilient metal alloy having a diameter in the order of one millimeter. The arcuate zone is employed to dislodge food or debris from pockets or interproximal spaces at both the mesial and distal areas of the oral cavity with the tip functioning as a probe. The convex surface of the arcuate zone is employed as a burnishing implement for the removal of soft plaque.

5 Claims, 6 Drawing Figures

U.S. Patent    Apr. 27, 1982    4,326,548
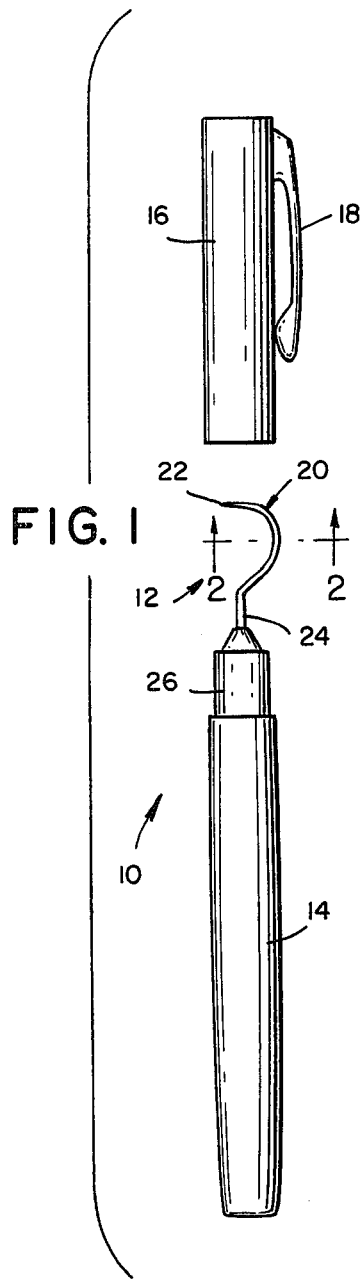
FIG. 1
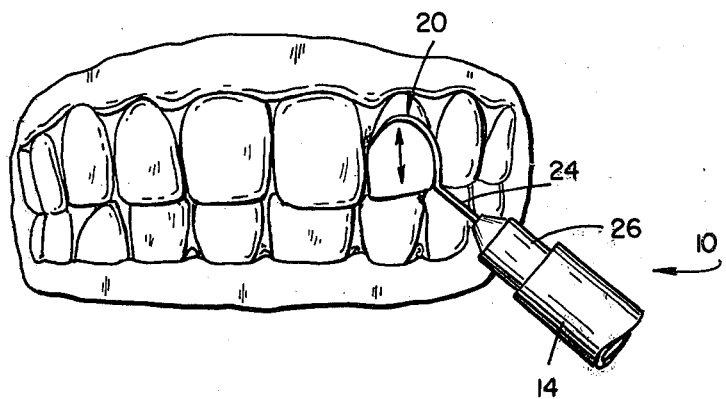
FIG. 6
FIG. 2
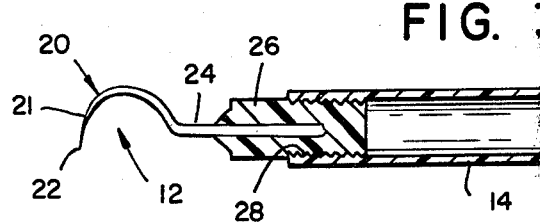
FIG. 3
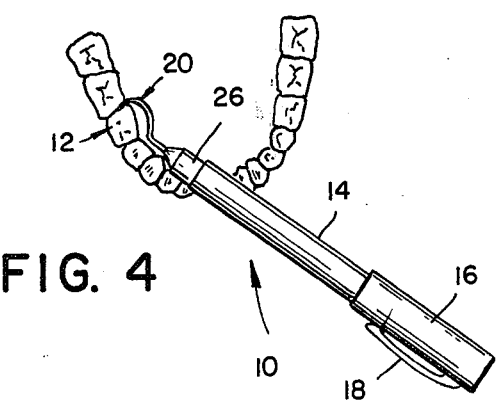
FIG. 4
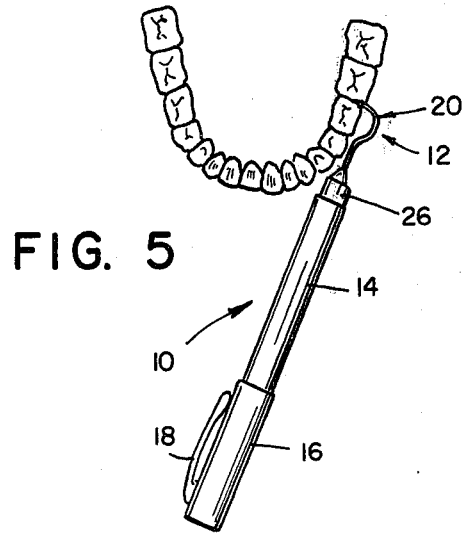
FIG. 5

PERSONAL ORAL HYGIENE TOOL

BACKGROUND OF THE INVENTION

1. Field of the Invention

This invention relates generally to oral hygiene appliances and more particularly to devices for removing particles of food from interproximal spaces between teeth as well as other oral areas wherein food or debris may collect.

2. Brief Description of the Prior Art

It has been established that food impaction has been a causative factor relating to both bone and periodontal diseases. In the past, personal oral hygiene has been limited to the use of relatively few cleansing devices. The most common personal oral hygiene device in use today is, of course, the common toothbrush. Toothbrushes preferably carry synthetic bristles and are used in conjunction with an abrasive agent such as toothpaste, tooth powder, baking soda and the like. Most people have encountered numerous occasions wherein tooth brushing has been insufficient to dislodge food particles caught in various pockets and interproximal spaces. Typical of such occurrences has been the lodgement of food particles in the mouth when eating such foods as corn on the cob, steak, roast beef, etc. In such instances, toothpicks have been the implements commonly resorted to. Unfortunately, toothpicks lacked the strength necessary to be wedged into tight interproximal spaces and often splintered. In addition, toothpicks were difficult to manipulate at the molar areas.

An alternate prior implement has been dental floss. Dental floss provided a greater cleansing effect than toothpicks and was considered to be safer than toothpicks. Dental floss has been effectively used for the cleansing of interproximal spaces between the teeth in the mesial area of the user's mouth. When food was lodged between the teeth in the distal area, between molars for example, the manipulation of dental floss for effective cleansing proved to be an arduous task.

An early attempt at providing a permanent, relatively strong, cleansing implement for the removal of debris from interproximal areas was illustrated in U.S. Pat. No. 435,350. In this patent, a folding pocket knife construction was employed for a toothpick having a sharply pointed, yet relatively thick, probe or gaff which extended perpendicular to the axis of a shaft. The shaft was, in turn, pivotally secured to a handle.

It was readily apparent that this device did not achieve universal usage, possibly due to the fact that the broad area of the probe was too thick to permit the user to wedge the device in interproximal areas. Furthermore, the sharply pointed probe extended a considerable distance beyond the axis of the shaft. As such, it presented a potential safety hazard which could inadvertently impale the user's gingiva or buccal surfaces, especially when handled by inexperienced users who could not observe the placement and manipulation of the gaff.

Other devices have been suggested for use in dislodging food particles. Examples of such other devices include electrically operated pumps which provided a pulsating jet of liquid for impingement against the user's gums and interproximal spaces between teeth for the purpose of oral hygiene. Not only were these devices relatively expensive, but they often lacked the necessary pressure to dislodge tightly wedged particles. In addition, they lacked the ability to be carried about by the user. Thus, when people were eating away from home and it was necessary to remove lodged food particles, these devices were not available.

SUMMARY OF THE INVENTION

In compendium, the invention comprises a portable personal dental cleansing tool which includes a curved resilient metal pick adapted for convenient manipulation in the mesial and distal areas of the user's mouth for the removal of food particles or debris. The pick is formed with an arcuate zone having a tapered tip. Opposite the tip, the pick includes an axial stem which is mounted in a holder. The pick stem may be seated within a cylindrical carrier with the carrier removably secured to the holder. The pick and its carrier may thus comprise a replaceable unit.

The arcuate zone of the pick is of relatively small diameter, e.g. one millimeter, and may be conveniently manipulated into interproximal spaces, pockets, and various traps formed by bridgework, orthodontic appliances and the like. The convex surface of the curved zone can be employed as a burnishing implement for the removal of soft plaque from the user's teeth.

In accordance with the present invention, the pick holder is shaped to simulate a pen barrel or other writing implement with a removable cap which selectively protects and conceals the tip. Thus, a user may inconspicuously carry the tool in a pocket or purse and, when the need for its use arises, it will be readily available.

From the foregoing summary, it will be appreciated that it is an object of the present invention to provide a personal oral hygiene tool of the general character described which is not subject to the disadvantage aforementioned.

A further object of the present invention is to provide a personal oral hygiene tool of the general character described which can be inconspicuously carried for use wherever needed.

Another object of the present invention is to provide a personal oral hygiene tool of the general character described which is well suited for the easy removal of food particles at the usually inaccessible distal area of the user's mouth.

Yet another object of the present invention is to provide a personal oral hygiene tool of the general character described which is suitable for both the dislodgement of food and for the removal of plaque.

Another object of the present invention is to provide a personal oral hygiene tool of the general character described which is efficient yet low in cost and suitable for economic mass production fabrication.

A further object of the present invention is to provide a personal oral hygiene tool of the general character described which presents the inconspicuous appearance of a writing implement when not in use.

Further objects of the present invention in part will be obvious and in part will be pointed out hereinafter.

With these ends in view, the invention finds embodiment in certain combinations of elements and arrangements of parts and series of steps by which the said objects and certain other objects are attained, all as more fully described with reference to the accompanying drawings and the scope of which is more particularly pointed out and indicated in the appended claims.

BRIEF DESCRIPTION OF THE DRAWINGS

In the accompanying drawings in which is shown one of the various possible exemplary embodiments of the invention:

FIG. 1 is an elevational view of a personal oral hygiene tool constructed in accordance with and embodying the invention and depicted with a cap removed from a pen barrel shaped holder to reveal a curved metal pick;

FIG. 2 is a greatly enlarged sectional view through an arcuate zone of the pick, the same being taken substantially along the line 2—2 of FIG. 1;

FIG. 3 is a fragmentary sectional view through the holder, the same being taken along a plane extending through the longitudinal axis of the holder parallel to the plane of FIG. 1 and illustrating the manner in which a stem of the pick is secured in a thermoplastic carrier which is in turn seated in the holder;

FIG. 4 is a plan view of teeth positioned in the lower jaw of a typical user's mouth and illustrating the manner in which the tool is manipulated for the purpose of dislodging food particles wedged in an interproximal space between a first bicuspid and a first molar and showing the pick being advanced into the interproximal space employing a lingual approach;

FIG. 5 is a further plan view of teeth positioned in the lower jaw of the user's mouth and showing the tool being employed for dislodging food particles from a similar interproximal space using a buccal rather than a lingual approach and;

FIG. 6 is an enlarged front elevational view of a typical user's mouth and illustrating the manner in which the convex portion of the curved pick is used as a burnishing tool for the purpose of removing soft supergingival plaque.

DESCRIPTION OF THE PREFERRED EMBODIMENT

Referring now in detail to the drawings, the reference numeral 10 denotes generally a dental tool constructed in accordance with and embodying the invention. The tool 10 comprises a curved metal pick 12 employed for the cleansing of food or debris from pockets or interproximal spaces at both mesial and distal areas of the oral cavity. The pick 12 is secured to a hollow cylindrical holder 14 and projects from one end thereof. The end of the holder 14 from which the pick 12 projects is selectively covered by a cap 16 which may include a conventional pocket clip 18.

In accordance with the present invention, the dental tool 10 may be inconspicuously carried about the person of the user and maintains the general appearance of a writing implement such as a pen. For this purpose, the holder 14 is shaped in simulation of a pen barrel and the cap 16 in simulation of a pen cap. As shown in FIGS. 4 and 5, when the tool 10 is in use the cap 16 may be conveniently positioned over the opposite end of the holder 14 to provide a handle extension which is readily manipulatable by the user.

Referring now to FIGS. 1 and 3 wherein the pick is illustrated, it will be seen that the pick 12 includes an arcuate zone 20 similar in configuration to a limacon section. The arcuate zone 20 terminates at a forward probe 21 having a tapered tip 22. At the opposite end, the curvature is somewhat reduced and the arcuate zone 20 approaches a stem 24 at an angle of approximately 45 degrees.

Pursuant to the present invention, the pick 12 is formed of a resilient stainless metal such as a stainless steel or a similar alloy. In the arcuate zone 20 including the probe 21, the pick is of circular transverse cross-sectional configuration as shown in FIG. 2 and is relatively thin, having a diameter in the order of 1 millimeter. This diameter has been found suitable for insertion within interproximal spaces without generating excessive lateral forces.

As such, it should be appreciated that the tapered tip 22 and the forward portion of the arcuate zone 20 will pass within the interproximal spaces between teeth adjacent the gingiva for the purpose of dislodging impacted food or debris. The resistance normally encountered when attempting to force a thicker toothpick or the like into the same area will not be encountered and the insertion force applied will only be that required to expel the impacted material rather than a force required to spread adjacent teeth apart.

Preferably, the entire pick 12 is formed of one piece and may lie within a single plane. At the stem 24, the diameter or thickness of the pick may be increased for strengthening purposes, i.e. to resist fatigue failure and to provide the desired degree of resiliency. It should be appreciated that, while the entire pick is illustrated as lying within a single plane, the arcuate zone 20 of the pick may be canted in an angular, spiral or helical configuration if desired.

From an observation of FIG. 3, it will be seen that the pick 12 is secured in a cylindrical carrier 26. The carrier may be formed of any suitable material such as metal or thermoplastic. Any conventional securement between the stem 24 and the carrier 26 may be provided. For example, a mating threaded connection or adhesive material may be employed. As shown in FIG. 3, the carrier may also be injection molded around the stem.

The outer surface of the carrier adjacent the end distant from the pick 12 includes an externally threaded zone 28. The threads of the zone 28 are adapted to mate with a corresponding internal threaded zone formed at an end of the holder. It should be appreciated that the pick 12 mounted to its carrier 26 comprises a single user replaceable unit. As such, in the event the user desires to replace the pick, such replacement can be easily accomplished.

Pursuant to the present invention, the shape of the pick 12 has been dictated by anatomical factors to permit a user to employ the tool for effective personal oral cleansing at both the mesial and distal areas of the oral cavity. Accordingly, the arcuate zone 20 is specifically configured to provide a contour readily adaptable to be positioned around the sides and/or cusps of the user's teeth in the distal areas of the oral cavity. The dimensional criteria of the arcuate contour fall within an average range of values.

Referring again to FIG. 3, the span of the arcuate zone as measured along the axis of the stem 24 may average from approximately ten millimeters to fifteen millimeters ($\frac{1}{4}$ inch to $\frac{3}{8}$ inch). Furthermore, it is desirable that the forward area or probe 21 terminate at the stem axis or that the tip 22 project beyond the axis of the stem 24 only a nominal distance, e.g. up to three millimeters ($\frac{1}{8}$ inch).

As previously discussed, with the cap 16 seated over the pick 12 and engaging the carrier 26, the tool 10 assumes the inconspicuous appearance of an ordinary writing implement and may be carried about in the user's pocket, purse or the like. Thus, the pick 12 will be readily available whenever the user is faced with the dilemma of the need to remove impacted food or debris which is lodged in interproximal areas, pockets, under bridgework, orthodontic appliances, etc.

When the lodged particle is caught or maintained in the mesial area of the user's oral cavity, the particle may be easily dislodged with the user applying the tapered tip 22 and the probe 21 to remove the particle. It will be appreciated that the probe 21 extends substantially perpendicular to the axis of the stem 24, and the user need only grasp the holder 14 and direct the tip 22 at the appropriate areas in need of cleansing. In many instances, it is beneficial for the user to employ a mirror to facilitate proper placement of the pick 12.

In instances where the desired cleansing is at the distal areas of the user's oral cavity, for example, between a cuspid and a first bicuspid or between a bicuspid or a molar or between molars themselves, the particular anatomical configuration of the pick 12 renders the removal of the lodged particle a relatively simple task which does not require dexterity and which may be accomplished by the user without the assistance of other parties.

In FIG. 4, the tool 10 is illustrated during a typical procedure for the removal of matter wedged in an interproximal space between a first molar and a second molar. In the technique illustrated, the user has selected a lingual approach for the removal of the lodged matter and has applied the pick 12 to the appropriate interproximal space from the lingual side urging the tip 22 and the probe 21 into the interproximal space in a buccal direction.

It should be appreciated that the dimensions of the arcuate zone 20 readily accommodate the curved surfaces of the first molar and the probe 21 may be inserted into the interproximal space to free the lodged matter without interference from the adjacent first bicuspid. Little, if any, resistance to the insertion of the probe 21 will be encountered since the diameter of the pick is preferably accommodatingly received within the interproximal space.

In FIG. 5, an alternate procedure for removal of lodged matter in a similar area of the user's mouth is shown. In this procedure, the user has inserted the probe 21 into an interproximal space from the buccal rather than lingual side. It should be appreciated that the particular approach employed is a matter of personal preference to the user except in instances wherein the lodged material cannot be reached readily with a preferred approach.

In FIG. 6 a method of employing the tool of the present invention for the removal of soft plaque is illustrated. By way of example only, the tool is shown in the process of removing supergingival soft plaque from a lateral incisor. This procedure entails employing the exterior convex surface of the arcuate zone 20 as a burnishing implement in a reciprocal vertical movement against the tooth while at the same time applying a light lateral pressure. It has been found that a rounded smooth, yet resilient, metal such as the convex surface of the arcuate zone 20 is quite effective for the removal of soft plaque and may be quite beneficial when routinely employed as part of an oral hygiene program.

The personal oral hygiene tool of the present invention is adapted for an individual's personal use. It may be readily cleansed for hygienic purposes and/or easily sterilized with a swab or gauze pad impregnated with alcohol or other germicidal agent.

Thus, it will be seen that there is provided a personal oral hygiene tool which achieves the various objects of the present invention and which is well adapted to meet the conditions of practical use.

Since various possible embodiments might be made of the present invention and since various changes might be made in the exemplary embodiment set forth herein, it is to be understood that all matter shown in the accompanying drawings or described herein is to be interpreted as illustrative and not in a limiting sense.

Having thus described the invention, there is claimed as new and desired to be secured by Letters Patent:

1. A dental tool for personal oral hygiene comprising a pick, the pick having a stem and an arcuate zone projecting from the stem and terminating at a tip, the tip extending along a plane substantially perpendicular to the axis of the stem and projecting beyond the stem axis a distance up to but not significantly greater than three millimeters, the pick being formed of a resilient material, the material having a diameter in the order of one millimeter at the arcuate zone and tapering to a smaller diameter at the tip, the stem diameter being larger than the material diameter at the arcuate zone, the arcuate zone being anatomically configured to be accommodatingly received around curved tooth surfaces and including a longitudinal span of between substantially ten to fifteen millimeters, the tip passing between interproximal spaces formed between adjacent teeth in the user's mouth with the pick contoured to avoid interference with adjacent teeth to thereby efficaciously remove materials lodged in such interproximal spaces, the tool further including an elongate cylindrical holder, means securing the pick at one end of the holder and a cap, the cap selectively covering the pick when not in use, the holder and the cap being configured in simulation of a writing implement whereby the tool may be inconspicuously carried about.

2. A dental tool for personal oral hygiene constructed in accordance with claim 1 further including a carrier, the means securing the pick to the holder including means mounting the stem to the carrier and means selectively securing the carrier to the holder, the pick and the carrier comprising a replaceable unit.

3. A method of removing material lodged in a user's mouth with a personal oral hygiene tool constructed in accordance with claim 1, said method comprising the steps of:
  (a) ascertaining the location of the lodged material,
  (b) removing the cap to expose the pick,
  (c) grasping the holder and rotating the holder to orient the tip and the arcuate zone adjacent the tip toward the lodged material,
  (d) removing the lodged material by applying lateral pressure to gently force the tip against the lodged material.

4. A method in accordance with claim 3 wherein the lodged material is located at a distal area of the user's mouth, the method further including the step of orienting the curvature of the arcuate zone to be coincident with a curved surface of the tooth immediately preceding the located material to avoid interference between the pick and the preceding tooth when the tip is urged laterally against the material.

5. A method in accordance with claim 3 further including the step of placing the removed cap over the opposite end of the holder before removing the lodged material.

* * * * *